United States Patent [19]

Troutner

[11] Patent Number: 4,681,568
[45] Date of Patent: Jul. 21, 1987

[54] VALVE APPARATUS FOR PHOTOACTIVATION PATIENT TREATMENT SYSTEM

[75] Inventor: Vernon H. Troutner, St. Petersburg, Fla.

[73] Assignee: McNeilab, Inc., Fort Washington, Pa.

[21] Appl. No.: 834,303

[22] Filed: Feb. 27, 1986

Related U.S. Application Data

[63] Continuation-in-part of Ser. No. 665,827, Oct. 29, 1984, Pat. No. 4,596,547.

[51] Int. Cl.⁴ .............................................. A61M 5/005
[52] U.S. Cl. ........................................ 604/250; 604/4
[58] Field of Search ........................................ 604/4–6, 604/30–34, 250; 251/9

[56] References Cited

U.S. PATENT DOCUMENTS

| | | | |
|---|---|---|---|
| 3,543,752 | 12/1970 | Hesse et al. | 604/250 |
| 3,575,161 | 4/1971 | London | 604/250 |
| 3,932,065 | 1/1976 | Ginsberg et al. | 604/34 |
| 3,994,294 | 11/1976 | Knute | 604/250 |
| 4,061,142 | 12/1977 | Tuttle | 604/34 |
| 4,282,902 | 8/1981 | Haynes | 604/250 |
| 4,596,547 | 6/1986 | Troutner | 604/250 |

*Primary Examiner*—Stephen C. Pellegrino
*Assistant Examiner*—Gene B. Kartchner
*Attorney, Agent, or Firm*—Mark A. Hofer

[57] ABSTRACT

Manually overridable servo controlled valve mechanisms for controlling the flow of fluids through a flexible tube for use in a photoactivatable agent treatment system wherein photoactivatable agents, in contact with patient blood cells, are irradiated extracorporeally and then returned to the patient.

7 Claims, 10 Drawing Figures

VALVE APPARATUS FOR PHOTOACTIVATION PATIENT TREATMENT SYSTEM

This application is a continuation-in-part of U.S. Ser. No. 665,827, filed Oct. 29, 1984, now U.S. Pat. No. 4,596,547.

FIELD OF THE INVENTION

This invention relates to the field of treating cells with photoactivatable compounds and radiation which activates the compound thereby affecting the cells and specifically, relates to clinically useful systems for the extracorporeal treatment of blood cells, especially leukocytes, with UV radiation and more particularly with automated, manual overridable valves therefor.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are through to be cleared by natural processes but at an accelerated pace believed attributable to disruption of membrane integrity, alteration of DNA within the cell, or the like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems require solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Ser. No. 650,602, describes a practical device for coupling the radiation provided by commercially available light sources, such as the so-called "black-light" fluorescent tubes, to cells for treatment by Edelson's photoactivated drug methods. In summary, the disposable cassette described therein comprises a plurality of fluorescent tube-like light sources such as the U.V.A. emitting Sylvania F8T5/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to U.S. Ser. No. 650,602.

To be fully practical, the Taylor device requires a clinically acceptable instrument to house the device and to provide the cells to be treated in an appropriate form. Such an instrument is the object of the inventions described in U.S. Pat. Nos. 4,573,960, 4,568,328, 4,578,056, 4,573,961, 4,596,547, 4,623,328 and 4,573,962, fully incorporated herein by reference. While the instruments described therein work well, it is an object of the instant application to describe improved systems capable of implementing, in advanced fashion, the medical treatment principles first taught by Edelson.

It is another object of the present invention to provide still further improvements in greater patient safety and comfort while reducing treatment time and cost, by utilizing a newly designed disposable irradiation chamber in an appropriate instrument which incorporates a photoactivating light array, more fully described in copending applications U.S. Ser. No. 834,258 and U.S. Ser. No. 834,256, respectively.

It is yet another object to provide an improved instrument which meets the above criteria along with all the positive attributes of the prior system; compactness, mobility, completeness, fully automated and monitored, coupled with ease of operation.

It is a further related object of this invention to provide, in contrast to the time consuming batch like processing of the prior system, continuous on-line patient treatment wherein collection, separation, and cell treatment occur simultaneously, thereby reducing treatment time and increasing patient safety and comfort.

BRIEF DESCRIPTION OF THE DRAWINGS

These and still other objects of the invention will become apparent upon study of the accompanying drawings wherein.

FIG. series 4 shows a pivoting "or" valve of the present invention;

FIG. series 5 shows a pivoting "on/off" valve of the present invention;

SUMMARY OF THE INVENTION

In accordance with the principles and objects of the present invention there are provided apparatus for "online" extracorporeally photoactivating a photoactivatable reagent in contact with blood cells by collecting and separating on a continuous basis, blood from a patient while the patient is connected to the apparatus, returning undesired blood portions obtained during separation while the desired portion is photoactivatably treated whereupon the thusly treated cells are returned to the patient. As a result of this novel approach, the treatment system of the instant inventions optimizes and minimizes treatment time by concurrently conducting various aspects of such photoactivation treatment which were previously performed sequentially. More specifically, the apparatus collects and separates blood on a continuous basis as it is withdrawn from the patient and returns unwanted portions to the patient while concurrently energizing the irradiation sources for photoactivating the photoactivatable reagent in contact with the desired blood portion. Following photoactivation, the treated cells may then be facilely returned to the patient utilizing a drip chamber gravity feed infusion line incorporated in the tubing set. As will be readily apparent, the system of the instant invention requires a tubing set connecting the patient to the system and for conveying various blood portions to specified areas for manipulation. Fluid flow control is accomplished by new valve mechanisms which are the particular subject of this invention. These valve mechanisms are servo controlled but manually overridable.

DETAILED DESCRIPTION

Figure 1:
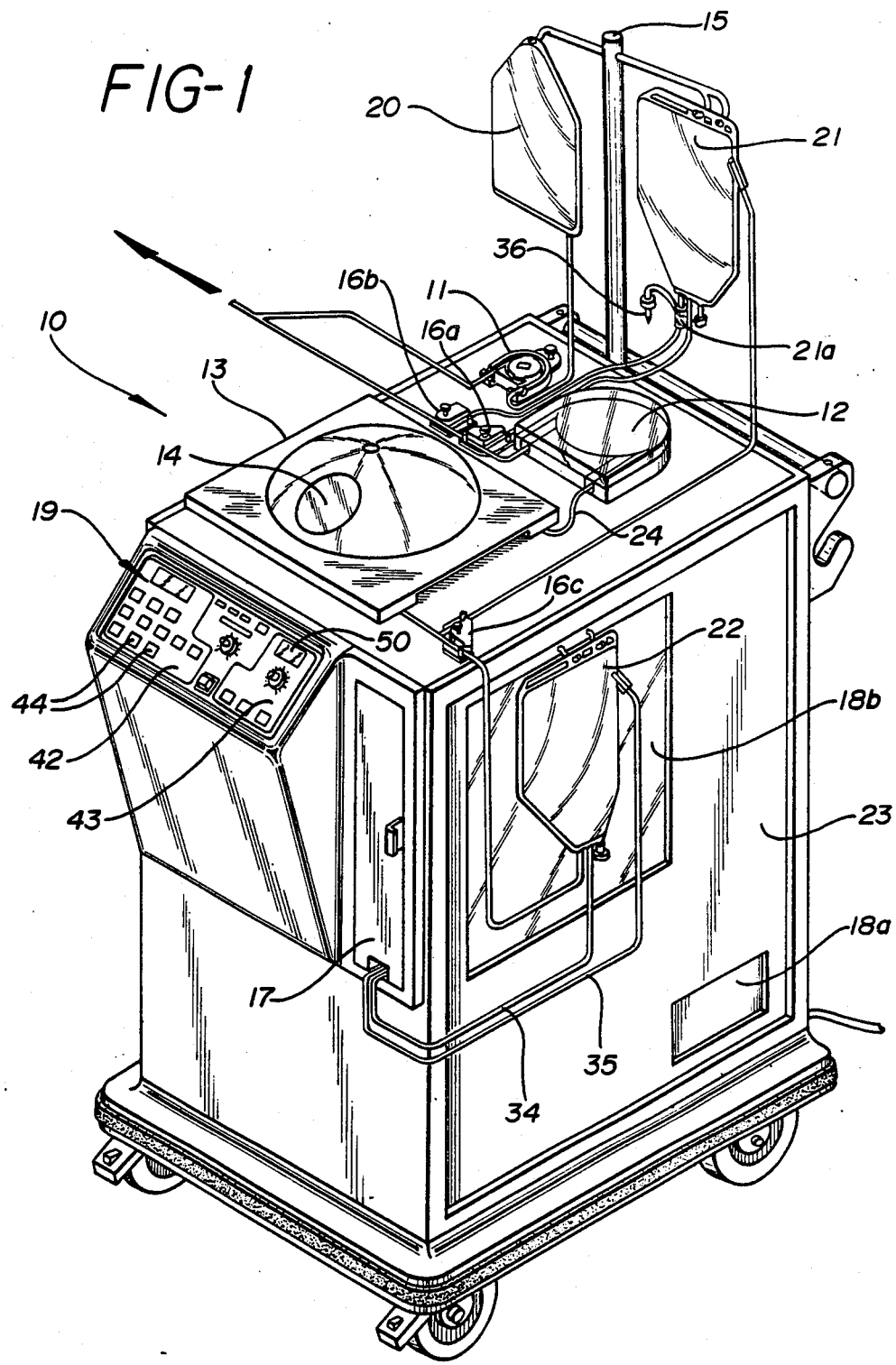
FIG. 1 illustrates a preferred configuration of the system during collection, separation, and treatment.
Figure 2:
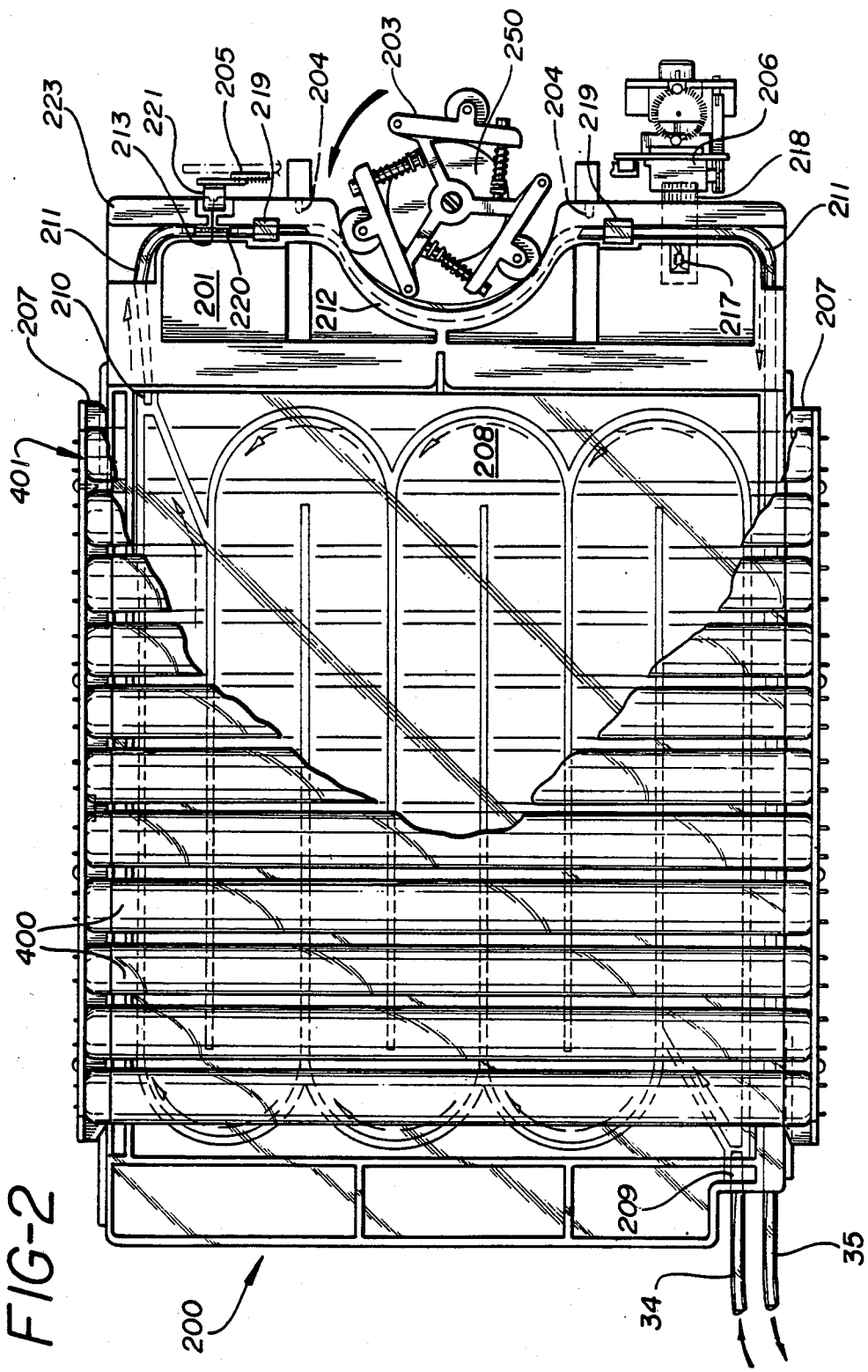
FIG. 2 shows a preferred embodiment of the flat plate irradiation chamber, recirculation pump, and photoactivating light source array.
Figure 3:
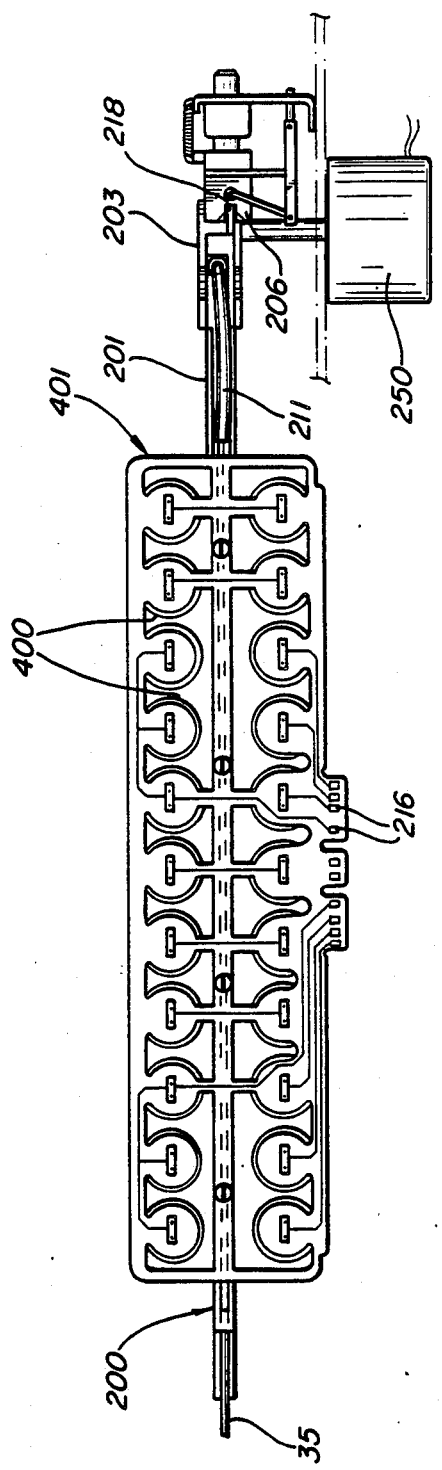
FIG. 3 shows a bottom view of the structures of FIG. 2.

FIG. 1 shows various aspects of the system developed for extracorporeally treating a patient based in part upon the scientific discoveries of Edelson. While the specific design, construction and operation of the apparatus 10 is the result of a number of separate inventions some of which form the subject matter of previously described issued patents and copending commonly assigned applications including U.S. Ser. No. 834,292 entitled "Concurrent On-Line Irradiation Treatment Process"; U.S. Ser. No. 834,293 entitled "Electronic Device For Authenticating And Verifying Disposable Elements"; U.S. Ser. No. 834,294 entitled "Disposable Temperature Probe For Photoactivation Patient Treatment System"; U.S. Ser. No. 834,256 entitled "Light Array Assembly For Photoactivation Patient Treatment System"; U.S. Ser. No. 834,257 entitled "Pump Block for Interfacing Irradiation Chamber to Photoactivation Patient Treatment System"; U.S. Ser. No. 834,260 entitled "Demountable Peristaltic Pump For Photoactivation Patient Treatment System"; U.S. Ser. No. 834,259 entitled "Zero Insertion Force Socket For Photoactivation Patient Treatment System" and U.S. Ser. No. 834,258 entitled "Irradiation Chamber For Photoactivation Patient Treatment System", the relevant parts of which are fully incorporated herein by reference, nonetheless it is believed a brief description may be helpful.

The operation of the device and performance of the methods can be divided into two basic phases or modes, depicted in part by FIG. 1. The first phase is shown substantially in FIG. 1 wherein the patient is connected at the point shown, preferably by venipuncture or the like methods well-known and developed to a high degree in the dialysis arts. Patient blood, as it flows to the apparatus 10 (alternately referred to herein as the photopheresis apparatus or system) is preferably infused, under control of pump 11, with an anticoagulant agent contained in container 20 hung from stand 15. Control of the flow of patient blood to the remainder of apparatus 10 is controlled largely by clamping means 16a which has the dual function of also controlling flow in the reverse direction as well as flow to return container 21. Clamp 16a acts as an "or" valve and will be described in greater detail later.

Normally the blood flows through tubing 24 through blood pump 12 (preferably a roller pump such as that described in U.S. Pat. No. 4,487,558 to Troutner entitled "Improved Peristaltic Pump" and incorporated herein by reference) into continuous centrifuge 13. This continuous centrifuge, available commercially from suppliers such as Dideco, Haemonetics and others, is preferably capable of continuously separating blood based on the differing densities of the individual blood components. "Continuously", as used herein means that, as blood flows into the centrifuge through line 24, it accumulates within the rotating centrifuge bowl and is separated so that low density components are emitted after a certain minimum volume has been reached within the centrifuge bowl and as additional blood is added. Thus, the continuous centrifuge in effect acts as a hybrid between a pure online system and a pure batch system. This occurs because the centrifuge bowl has a capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained. Prior to that point, the operator, by viewing the uppermost portion of the centrifuge bowl through the centrifuge cover, can detect qualitatively when the centrifuge emits plasma (as opposed to priming solution), leukocyte enriched portions and the remainder, i.e., nonleukocyte enriched portions, including erythrocyte enriched portions. Based on the operator's observations, he or she enters through control panel 19 the identification of the individual blood portions as they are emitted from the centrifuge. This information is entered by keys 44 (e.g. PLASMA, BUFFY COAT or leukocyte enriched portion) on control panel 19, and in response thereto, the apparatus 10 controls valve mechanism 16c to direct the leukocyte enriched portion and a predetermined volume of plasma into plasma-leukocyte enriched container 22 while excess plasma, air, priming fluids, erythrocytes etc. are directed to container 21.

Once the centrifuge is no longer capable of further separation due to the attainment of its capacity, the operator directs that the bowl be emptied by suitable data key entry on panel 19 and the fluid contents of centrifuge 13 are advantageously pumped into return container 21 by means of pump 12 under the control of valves 16a and c. The foregoing steps may be repeated a number of times or cycles before the desired volume of leukocyte enriched blood and plasma is obtained for further treatment, in each instance the undesired portions being collected in return container 21.

Between cycles, the fluids, including erythrocytes which have been pumped into return bag 21 are gravity fed back to the patient through a drip infusion operation and controlled by valve 16b. It is preferred that gravity feed be employed rather than pumping the blood back to the patient via pump 12 in order to avoid potential pressurization problems at the infusion insertion site at the patient, and also to avoid foaming or other air related dangers.

As may be already appreciated, when initially set up, the centrifuge bowl and line 24 may be expected to contain sterilized air which is preferably removed by suitable priming operations advantageously accomplished by utilizing the anticoagulation agent in container 20; both the air and a portion of priming solution being collected in container 21.

Also to be noted is the predetermination of the desired leukocyte enriched volumes and plasma volume to be collected within container 22 as well as the number of cycles to be employed to collect same. These volumes are selected largely in accordance with the individual volume capacities of the containers as well as the treatment irradiation chamber to be described later. Accordingly, these volumes are set in order to preferably optimize handling efficiency and to ensure patient safety. For instance, one preferred selection would include the following settings: 250 ml total buffy coat or leukocyte enriched portion and 300 ml of plasma to be collected within container 22. This might require any number of cycles, preferably on the order of three or four, bearing in mind that the more cycles that are selected, the lower the total volume of blood withdrawn from the patient at any one time. If blood collection meets the minimum capacity limits of the centrifuge bowl, the patient's capacity to withstand temporary blood volume depletions and the treatment procedure in general is increased.

Further, more cycles will permit more discriminating selection of leukocyte enriched blood as it is emitted from the centrifuge. The buffy coat and plasma volumes as well as the number of cycles are typically physician selected. Accordingly, the controls governing these selections are preferably placed within the apparatus 10, such as behind door 18a where their inadvertent alteration may be advantageously avoided, especially since no operator interaction is normally required with respect to these data inputs.

The leukocyte enriched container 22 is connected via tubing line 34 to the flat plate treatment chamber behind chamber assembly door 17 with a return line 35 to reservoir container 22.

The leukocyte enriched blood, plasma, and priming solution contained in reservoir 22 is delivered through line 34 to the inlet of the flat plate irradiation chamber 200, upward through the flat plate cavity in the chamber to the outlet. Tubing from the outlet passes through a pump block, affixed to the end of the flat plate irradiation chamber, and then connects to return line 35 which returns fluids from the chamber to container 22. A recirculation roller pump-type rotor, located internally in the machine, engages the tubing in the pump block in the semi-circular tract and thereby provides and controls the recirculating flow of fluid from container 22 up through the flat plate irradiation chamber and back to container 22. The tubing line associated with the flat plate irradiator preferably incorporates a thermocouple for monitoring the fluid temperature.

Sterile air, initially contained in the irradiation chamber cavity is advantageously displaced by entering fluid and stored in the top portion of container 22. By reversing the rotation of recirculation roller pump rotor, the air stored in container 22 can be pumped back into the outlet of the irradiation chamber thereby displacing all fluids back into container 22. When the irradiation chamber is fluid filled and the BUFFY COAT button on panel 19 is pressed, the light array assembly which surrounds the chamber is energized. Continued operation of the recirculation roller pump rotor results in recirculation of the leukocyte enriched fluid from container 22 through the chamber and the energized light array assembly and back to container 22. Thus, the photoactivating irradiation of the leukocyte enriched fluid is initiated at the outset and continues through and after the collection and separation process.

The flat plate irradiation chamber treatment element is described in greater detail in copending application U.S. Ser. No. 834,258, which is fully incorporated herein by reference.

In operation, the exposure time is set via panel 19 in accordance with physician determined criteria. The central control means of the apparatus 10 calculates and displays via central processing unit and memory stored software, the exposure time remaining at the onset of irradiation treatment and as the treatment progresses. Another portion of the control panel 19 also preferably includes three operator controlled entry data keys whereby the operator can de-energize the light array and stop the recirculation process if desired. Actual photoirradiation treatment commences automatically under control of the central processing unit when fluid is first directed to container 22. The leukocyte enriched portion of the blood collected within container 22, is pumped through tubing set 34, through the treatment cassette, through return line 35, and back into reservoir 22. This continues until the preset exposure time has expired whereupon the light array is de-energized and the recirculation roller pump reverses emptying the contents of the irradiation cassette into container 22.

Thereafter container 22 is ideally removed to stand 15 where it is connected to tube 36 provided on the drip chamber 21a, associated with return container 21, for reinfusion of the treated blood portion into the patient.

To further decrease the risk of contamination to the patient blood and blood portions, each time a connection is made or broken, it is preferably only done once.

Thus, container 22 would ideally have four connection points or ports; one for the collection of the leukocyte enriched blood portion, two for connection to the flat plate irradiation cassette, and the fourth for connection to the drip chamber for reinfusion of treated blood to the patient.

The control panel 19 of the apparatus 10 is shown with the keyboard entry buttons 44, each ideally having a light which, when lit, preferably indicates the stage of the operation. As will be noted, the keyboard entry buttons 44 are preferably placed in sequential order thereby assisting the operator in learning the system and performing the steps in the correct order. Indeed, the central control microprocessor will preferably be programmed to prevent out of step sequences from being implemented. A visual display indicates the volume of leukocyte enriched blood collected in container 22.

Panel 19 will preferably also contain a power switch, as well as a blood pump speed control whereby the operator may select the speed with which the blood is withdrawn from the patient and pumped through the system during collection. Also preferably included is an alpha-numeric display for indicating the machine's status and identifying alarm conditions throughout system operation. Optional accessory status lights, preferably provided in green, yellow, and red colors, provide at a glance the overall operating status of apparatus 10. Further included is a mute reset button for quieting an audible alarm activated in the event an alarm condition occurs and operator input is required.

Other features may be readily apparent from the drawings such as the preferable inclusion of casters and caster brakes for enhancing the mobility of the apparatus. Further, side panel 23 will preferably include mechanical means (e.g. hanging pegs and the like) for assisting in the securement of container 22. It may also optionally be outfitted with a transparent or translucent opening 18b in the area beneath container 22 for providing at a glance information regarding the illumination status of the irradiation treatment cassette during the treatment phase. For instance, if the window is of sufficient size, the operator may readily determine that each irradiation source within the treatment cassette is illuminated as desired. Naturally, the material comprising such window is preferably selected in order to contain harmful radiation, if any, within apparatus 10.

The aforedescribed photopheresis blood treatment apparatus is made largely possible by an automated control method for directing the blood portions, derived from the continuous centrifuge, into particular containers. The automated method performs in accordance with preset volume determinations which are manually entered behind panel 18a pursuant to a physician's direction. These predetermined volumes specify the volume to be contained within container 22 by setting forth the volume of plasma and the volume of leukocyte enriched blood portion to be directed thereto. Additionally included within these condition setting parameters is preferably the ability to set forth the number of cycles of blood collection and separation required or desired in order to obtain the desired blood volumes.

The volumes collected are determined in accordance with the blood volume pumped by the blood pump. This may be suitably monitored and communicated to the central control means by specifically monitoring the number of step pulses input to the pump to cause rotation of the blood pump. Typically, 200 pulses results in one revolution. Rotation may also be conveniently monitored such as by attachment of a slotted disk to the shaft and the passage of slots determined by an optical sensor means such as described in U.S. Pat. No. 4,623,328 (fully incorporated herein) and by monitoring shaft rotation. The resultant periodic signal may be conveniently correlated with speed and number of rotations by circuit designs well-known in the art. The number of rotations by any of the foregoing methods coupled "with the known volume pumping characteristics of the pump", will provide the necessary information regarding the volume of blood pumped. It will readily be appreciated that the sensors need not be optical but may be electronic or mechanical instead.

In actual operation, a most preferred procedure would be as follows. The operator presses the PRIME CENT. key on control panel section 19 which primes the tubing set, the blood pump, and the centrifuge with the anticoagulation solution contained in container 20. Displaced sterile air is collected in container 21. When priming solution emerges from the exit of the centrifuge, the operator presses PRIME UV key on control panel section 42 which closes the tubing line to container 21 and opens the tubing line to container 22 by means of valve 16c. Recirculation roller pump rotor 203 is energized to prime the flat plate irradiation chamber and collect displaced sterile air in container 22. The priming process stops automatically after a preset volume of fluid is delivered to container 22.

Blood collection is started by the operator pressing START key on control panel section 19. Thereafter, blood is withdrawn from the patient and pumped by the blood pump into the rotating centrifuge. As the blood enters the centrifuge, it displaces the priming solution which emerges first in accordance with its preferably lighter density. This priming solution is automatically directed into container 22 until a preset volume is delivered, after which the emerging solution is redirected to container 21 by means of valve 16c. At some point, the priming solution will be completely displaced from the rotating centrifuge and plasma will begin to emerge. This emergence may be directly observed through port 14 whereupon the operator presses the PLASMA key on control panel section 19. Thereafter, the central control means automatically directs the plasma into container 22 by altering valve 16c keeping track of the volume as it does so since the volume entering the centrifuge equals the volume emerging therefrom. This continues until the operator indicates the leukocyte enriched portion, i.e. buffy coat has begun by pressing the respective data entry key in control panel section 42 whereupon, the leukocyte enriched portion continues to container 22, however, the volume so directed is monitored as buffy coat volume. Alternatively, if all of the predetermined plasma volume is collected prior to the emergence of the buffy coat, then the central control means automatically diverts, by valve 16c, the emerging plasma fluid stream to container 21. In that instance, upon the emergence of the buffy coat and the keying of the BUFFY COAT data entry switch 44, the central control means diverts the emerging buffy coat into container 22 by means of valve 16c, again keeping track of its volume.

The collection of the buffy coat will preferably continue in accordance with both the predetermined buffy coat volume as well as the number of cycles, another condition predetermined by the physician. If this most preferred embodiment is employed, then a representative example might be as follows. Assume, that the predetermined volume and cycle conditions are set as follows: 350 mls of plasma, 250 mls of buffy coat, and 5 cycles. In each cycle, the apparatus will collect 250/5 or 50 mls of buffy coat before ending the cycle and thereupon emptying the centrifuge bowl and returning all nonleukocyte fluids, predominantly erythrocytes and perhaps excess plasma, to the patient. Prior to the collection of the 50 mls, plasma will emerge from the centrifuge and will be collected in container 22 either until the full 350 mls are collected or, until the buffy coat emerges.

During the next cycle, the central control means will direct the further collection of plasma, if needed, in order to reach the 350 ml predetermined volume and then collect an additional 50 mls of buffy coat. The total volume to be contained within container 22, will then equal 600 mls and would be indicated on display 46 as it is accumulated.

Thus, the instant invention serves to automatically keep track of the volumes as they are collected thereby facilitating the institution of a convenient number of cycles whereby the removal of large blood volumes from the patient is avoided. Not only is patient safety enhanced thereby, but the automated nature of the procedure further increases safety since, in accordance with the programmed conditions supplied to the central control microprocessor, the operator need not attempt to keep track of plasma and leukocyte enriched volumes collected, while still being assured that the final solution for treatment will contain the predetermined and desirable leukocyte concentration.

The foregoing described automated methods used in the photopheresis apparatus described with respect to FIG. 1 depends heavily upon the instant inventions for controlling fluid flow, in particular servo controlled valve mechanisms which may be manually overridden without disengaging the servo control means. These mechanisms are shown in Figure series 4 and 5 which describe the valve arrangements 16a, 16b, and 16c.

Figure 4A:
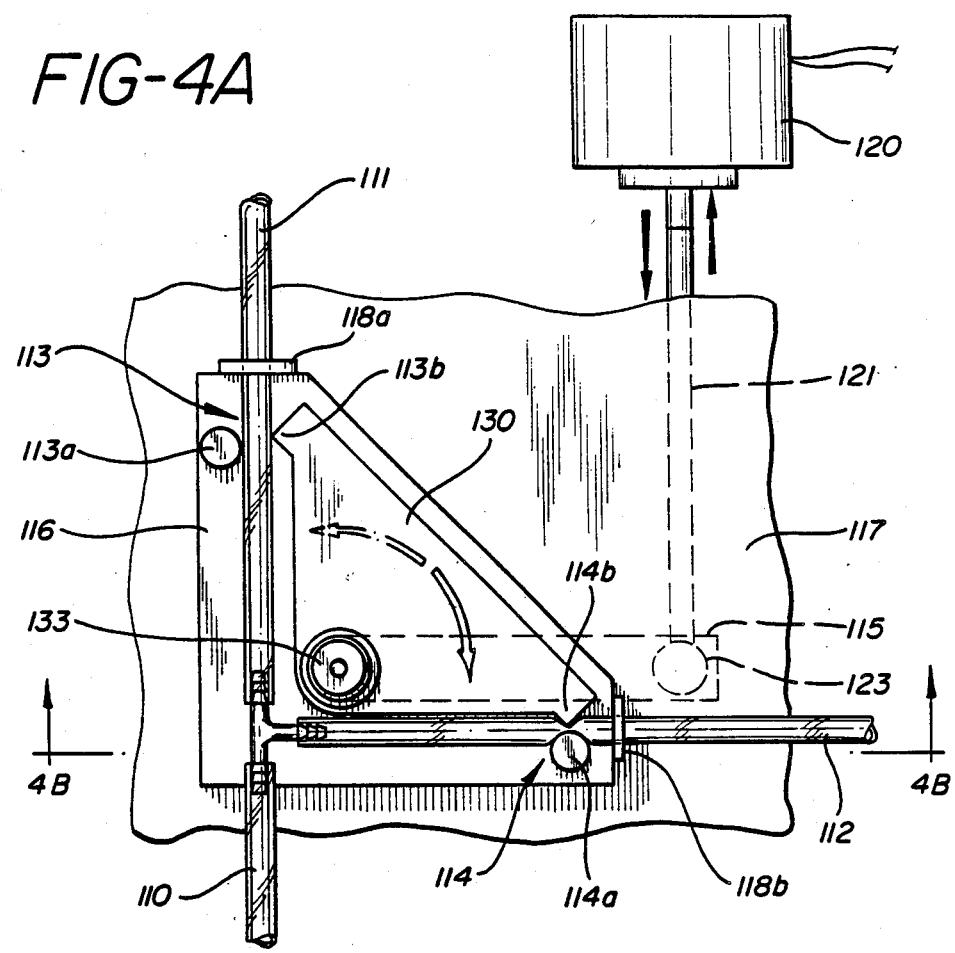
Figure 4B:
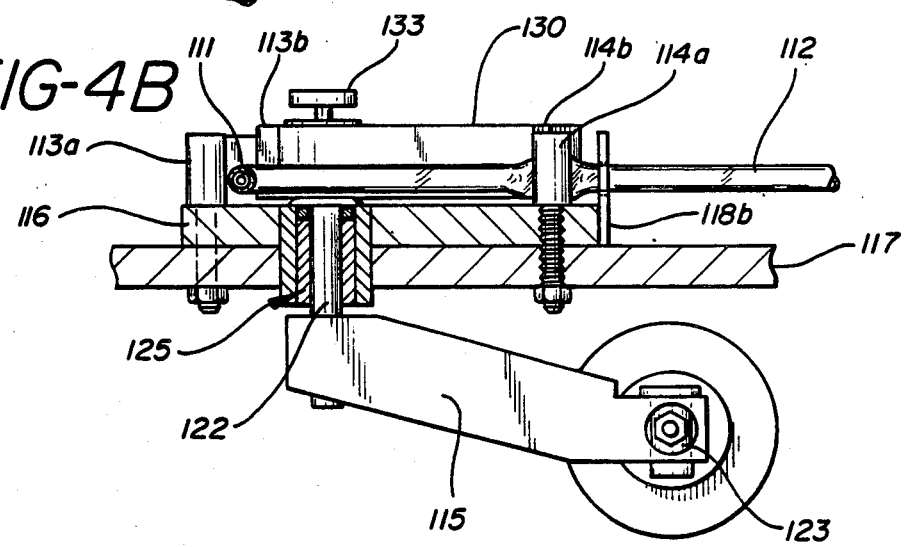

With specific reference to FIGS. 4a and b, depicted are top and side views of a pivoting "or" valve shown in FIG. 1 as 16a. Tubing portion 111 is connected to the patient and leads alternately to tubing 112 connected to the return container 21 (FIG. 1) and to tubing 110 which leads toward the blood pump 12 (FIG. 1). The tubing sections 111 and 112 rest against block means 116 which is fixedly mounted on work surface 117. Clamping means 130 is mounted on rotatable shaft 122 extending through bearing 125 which is mounted in fixed block 116. Clamp edges 113b and 114b operate alternately to squeeze tubing sections 111 and 112 respectively against fixed post or anvils 113a and 114a respectively. When activated, the respective clamping edges will preferably pinch the lines into full occlusion or permit free flow. Motion translator 115 is affixed to shaft 122. Actuator shaft 121 is pivotally mounted to the opposite end of the motion translator 115 by pivot means 123. Actuator shaft 121 is additionally attached to linear actuator stepper motor 120. Thus, inward and outward forces exerted by linear actuator stepper motor 120 are transmitted to clamp means 113 and 114 respectively. The clamp will optionally include slotted plates 118A and 118B, affixed to block 116, for advantageously retaining tubing 111 and 112 respectively in position for clamping.

As may be readily apparent, a manual override feature is desirable in order to facilitate the mounting and unmounting of tubing sets. The means for engaging and disengaging shaft 122 and clamping means 130 is shown in top view in FIG. 4C, and cut-away side view in FIGS. 4D and 4E. Shaft 122 is affixed to hollow cylindrical pivot block 126 which can rotate within cylindrical sleeve 127. Sleeve 127 is firmly affixed to clamping means 130. One or more juxtaposed holes 128a and 128b in sleeve 127 and pivot block 126 respectively, contain hard steel ball(s) 129. Also contained within the hollow pivot block 126 is plunger 131 having a narrow diameter portion 131a and a wide diameter portion 131b, and guide rod 131c. Compression spring 132 biases plunger 131 in an upward direction whereupon the wide diameter portion 131b aligns with balls 129 causing the balls 129 to enter holes 128a. In this position, shown in FIG. 4D, the balls 129 securely lock pivot block 126 together with sleeve 127 and all forces generated by linear actuator stepper motor 120 are transmitted through shaft 122 to clamp means 113 and 114. For operator comfort, button 133 is affixed to the extension of plunger 131. When button 133 is pressed, the plunger 131 moves downward against spring 132 until the narrow diameter 131a aligns with balls 129 allowing the balls 129 to move inward and exit holes 128a in sleeve 127. In this position, shown in FIG. 4E, the pivot block 126 is no longer locked to sleeve 127 and clamping means 130 is free to rotate. It is thus readily apparent that pressing button 133 will disengage the clamp from the actuator and permit easy installation or removal of tubing sets.

FIG. series 5 shows an "on/off" valve employed as valve 16b for controlling return flow from container 12 to the patient as well as for preventing inadvertent flow into container 21. As in FIG. series 4, the servo actuator motor 120 actuator shaft 121, and motion translator 115 are substantially the same although obvious mechanical variations may be substituted. In the "on/off" valve, however, although clamping means 140 and fixed block means 145 is rectangularly shaped rather than triangularly shaped, as in the FIG. 4 "or" valve, clamping edge 141b pinches line 143 against anvil 141a in a similar manner.

Figure 4C:
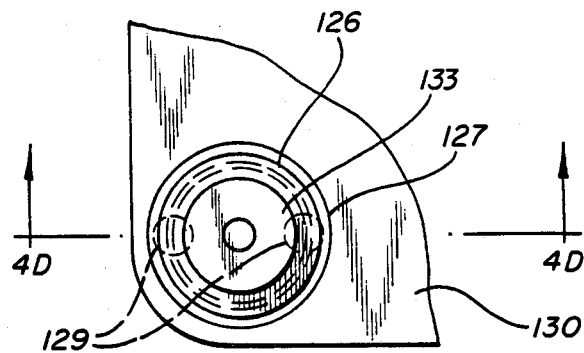
Figure 4D:
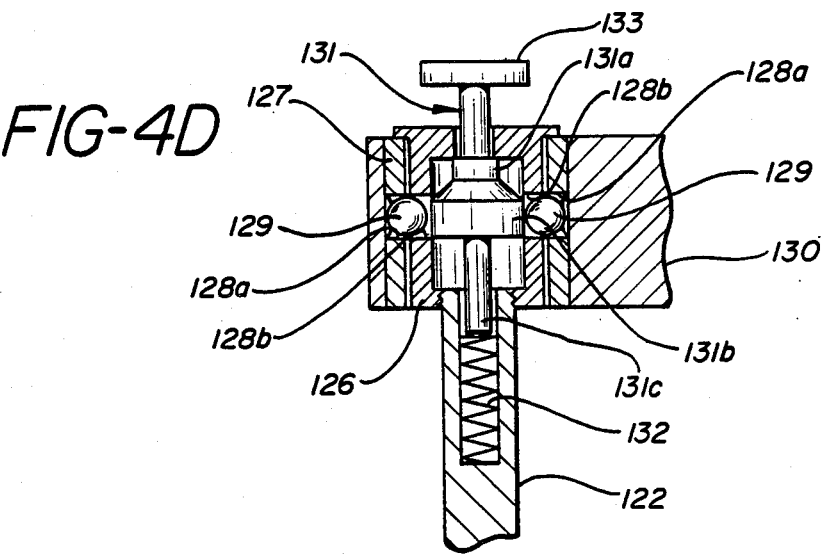
Figure 4E:
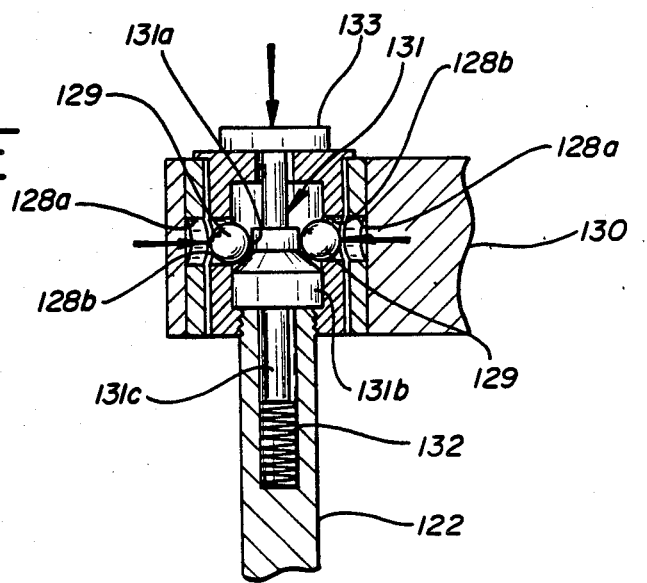
Figure 5A:
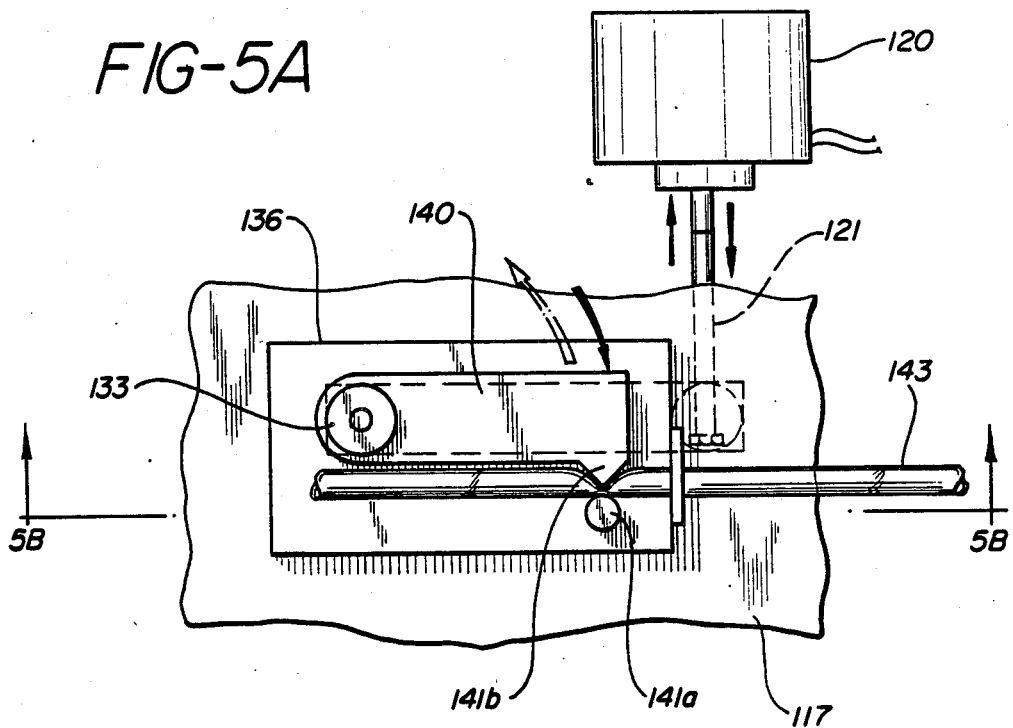
Figure 5B:
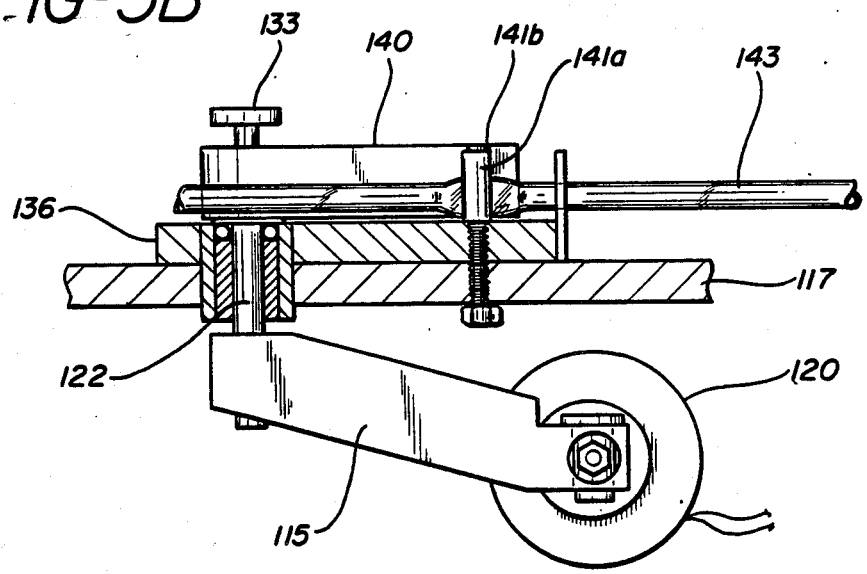

The disengaging mechanism shown in FIGS. 4C, 4D, and 4E may be identically used in the FIG. 5 on/off valve.

Upon study of the accompanying figures, and the foregoing description, it will become readily apparent to the skilled artisan that numerous alterations may be made to the foregoing without departing from either the spirit or scope of the instant invention.

What is claimed is:

1. Apparatus for controlling the flow of fluids through a flexible tube for use in a photoactivatable agent patient treatment system comprising:
   (a) actuator means for supplying force in response to a signal:
   (b) clamping means movably mounted on a work surface;
   (c) post means mounted on said work surface adjacent to said clamping means whereby flow through said flexible tube, placed therebetween, may be reduced by movement of said clamping means toward said post means thereby compressing said flexible tube;
   (d) motion translator means, associated with said clamping means through a manually disengagement rotation clamp means, for moving said clamping means in response to force supplied by said actuator means, wherein the manually disengageable rotation clamp means comprises,
(1) an outer collar and an inner collar rotatable therein, wherein the inner collar is fixedly associated with said motion translator means and said outer collar is fixedly associated with said clamping means;
(2) at least one locking element means associated with said inner collar and not said outer collar when said locking element means is in a first position, said locking element means associated with said inner and outer collar when in a second position wherein said locking element means is received by said outer collar, said association in said second position acting to prevent rotation of said inner collar in said outer collar;
(3) manually engageable locator means for moving said locking element means from said first position to said second position; and
(4) resilient biasing means for urging said locator means to move said locking element means to said second position whereby force supplied by said actuator means through said motion translator means is transferred to said clamping means and wherein movement of said locator means against said resilient biasing means allows said locking element means to move from said second position to said first position upon manual movement of said clamping means; and
(d) actuator bar means having one end connected to said actuator means and the other end associated with said motion translator means for communicating said actuator means supplied force to said motion translator means.

2. The apparatus of claim 1 wherein said clamping means includes at least two clamping means which move towards and away from said post means to cooperate, in an "or" configuration, to control the fluids through two flexible tubes, placed between said clamping means and said post means.

3. The apparatus of claim 1, wherein the actuator means is a linear actuator stepper motor.

4. The apparatus of claim 1, wherein the motion translator means is a shaft affixed to said rotation clamp means.

5. The apparatus of claim 1, wherein the locator means is a plunger comprising a narrow diameter portion, a wide diameter portion and a guide rod.

6. The apparatus of claim 1, wherein the actuator bar means is a bar connected to said actuator means and pivotally mounted to the end of said motion translator means.

7. The apparatus of claim 1, wherein the locking element means is a spherical ball which is received in a hole in said outer collar.

* * * * *